(12) United States Patent
Mitchnick

(10) Patent No.: US 7,175,611 B2
(45) Date of Patent: Feb. 13, 2007

(54) ANTIMICROBIAL RELEASE SYSTEM

(76) Inventor: Mark Alan Mitchnick, 80 Three Mile Harbor Dr., East Hampton, NY (US) 11937

( * ) Notice: Subject to any disclaimer, the term of this patent is extended or adjusted under 35 U.S.C. 154(b) by 500 days.

(21) Appl. No.: 10/163,628

(22) Filed: Jun. 5, 2002

(65) Prior Publication Data

US 2003/0229319 A1 Dec. 11, 2003

(51) Int. Cl.
*A61M 5/32* (2006.01)
*A61M 25/00* (2006.01)
*A61L 33/00* (2006.01)
*B05D 3/00* (2006.01)

(52) U.S. Cl. ..................... 604/265; 427/2.12
(58) Field of Classification Search ............... 604/264, 604/265, 266; 427/2.1, 2.11, 2.12, 2.24, 427/2.28, 2.3
See application file for complete search history.

(56) References Cited

U.S. PATENT DOCUMENTS

| | | | |
|---|---|---|---|
| 4,723,950 A | 2/1988 | Lee | 604/322 |
| 5,047,020 A * | 9/1991 | Hsu | 604/266 |
| 5,091,442 A | 2/1992 | Milner | 523/122 |
| 5,180,605 A | 1/1993 | Milner | 427/2 |
| 5,261,421 A | 11/1993 | Milner | 128/898 |
| 5,418,130 A | 5/1995 | Platz et al. | 435/2 |
| 6,168,601 B1 | 1/2001 | Martini | 606/90 |
| 6,224,579 B1 | 5/2001 | Modak et al. | 604/265 |
| 6,278,018 B1 | 8/2001 | Swan | 562/53 |
| 6,342,250 B1 | 1/2002 | Masters | 424/484 |
| 6,730,064 B2 * | 5/2004 | Ragheb et al. | 604/265 |
| 2002/0032414 A1 * | 3/2002 | Ragheb et al. | 604/265 |
| 2003/0036794 A1 * | 2/2003 | Ragheb et al. | 623/1.15 |
| 2003/0216524 A1 * | 11/2003 | Bide et al. | 525/418 |

FOREIGN PATENT DOCUMENTS

JP 03094762 * 4/1991

OTHER PUBLICATIONS

Curtis, T.P., et al., "Fate of *Cryptosporidium* oocysts in an immobilized titanium dioxide reactor with electric field enhancement" Water Research 36(2002) pp. 2410-2413.
XP-002251348, 2002, JP.
XP-009015675, Nov. 1999, JP.
XP-001154062, May 2001, JP.

* cited by examiner

*Primary Examiner*—Kevin C. Sirmons
*Assistant Examiner*—Mark K Han
(74) *Attorney, Agent, or Firm*—Mark A. Litman & Associates, P.A.

(57) ABSTRACT

The present invention relates to medical devices that are inserted or implanted into patients and that have antimicrobial coatings that release free radicals into the vicinity of the device. These devices may have coatings that alter their rate of flow release or elution release of an antibacterial agent from a coating on the device upon external stimulation. The coating should therefore be responsive to external control such as by heating, external RF stimulus, sonic control, visible or ultraviolet light exposure and the like. By having control of the release rate, and in some structures without invasion of the patient by mechanical means in addition to the device itself, the release rate can be in response to need at the implant site. The class of compounds to be released are free radical generating or initiating compounds, or compounds that release free radicals upon immersion or stimulation, the free radicals acting as the antimicrobial agent.

16 Claims, 1 Drawing Sheet

ANTIMICROBIAL RELEASE SYSTEM

BACKGROUND OF THE INVENTION

1. Field of the Invention

The present invention relates to the delivery of antimicrobial functions or agents from the surface of coatings, particularly the release of antimicrobial functions or agents from the surface of medical devices, especially medical devices that have been inserted or implanted into patients. The invention particularly relates to the controlled or controllable delivery of such functions or agents.

2. Background of the Art

It has become common to treat a variety of medical conditions by introducing or implanting a temporary or permanent medical device partly or completely into a patient. These devices may be inserted or implanted (the term "implanted" shall be used herein to reflect both short term insertion and long term implantation) into many different organs and glands such as the heart, brain, esophagus, stomach, trachea, colon, biliary tract, urinary tract, vascular system or other location within a human or veterinary patient. These implants may be in the form of a device such as a pump, delivery system, sensing system, stent, catheter, balloon, wire guide, cannula, electrical pulsing or pacing system or the like. However, when such a device is introduced into and manipulated through the vascular system or implanted at a selected site, the tissue or vascular walls can be disturbed or injured. Clot formation or thrombosis, bacterial collection and infection and other adverse events can occur at the injured site or implantation site, causing acute or chronic injury or infection at the sire. Moreover, if the medical device is left within the patient for an extended period of time, thrombus and infections may often form on the device itself, again causing serious potential for damage and illness. As a result, the patient is placed at risk of a variety of complications, including heart attack, pulmonary embolism, stroke, site infection, sepsis, implant rejection, and the like. Thus, the use of such a medical device can entail the risk of causing problems as serious or worse than the problems that the device's use was intended to ameliorate.

Another way in which blood vessels undergo stenosis is through disease. Probably the most common disease causing stenosis of blood vessels is atherosclerosis. Atherosclerosis is a condition which commonly affects the coronary arteries, the aorta, the iliofemoral arteries and the carotid arteries. Atherosclerotic plaques of lipids, fibroblasts, and fibrin proliferate and cause obstruction of an artery or arteries. As the obstruction increases, a critical level of stenosis is reached, to the point where the flow of blood past the obstruction is insufficient to meet the metabolic needs of the tissue distal to (downstream of) the obstruction. The result is ischemia.

Many medical devices and therapeutic methods are known for the treatment of atherosclerotic disease. One particularly useful therapy for certain atherosclerotic lesions is percutaneous transluminal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic) directly into the arterial wall at the time of angioplasty could reduce the incidence of thrombotic acute closure, but the results of attempts to do so have been mixed.

A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling." It has similarly been postulated that the delivery of appropriate agents directly into the arterial wall could interrupt the cellular and/or remodeling events leading to restenosis. However, like the attempts to prevent thrombotic acute closure, the results of attempts to prevent restenosis in this manner have been mixed.

Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae, pacemakers, defibrilators, pumps, eluent drug delivery systems and other devices inserted into organs such as the heart, the brain, the esophagus, the trachea, the colon, biliary tract, urinary tract and other locations in the body, or with orthopedic devices, implants, or replacements. It would be desirable to develop devices and methods for reliably delivering suitable agents, drugs or bioactive materials directly into a body portion during or following a medical procedure, so as to treat or prevent such conditions and diseases, for example, to prevent site infection, either from short term insertion or long term implantation of the device. As a particular example, it would be desirable to have devices and methods which can deliver an antibacterial agent or other medication to the region of implantation, where the release of the antibacterial agent can be externally controlled, rather than relying on predetermination of a release rate. Additionally, the release rate should not be dependent upon external reading of the device or regular sampling of the blood stream to determine when release rates of a medical pump should be modified to adjust to altering patient conditions. The antibacterial delivery system should also be minimally additive in size or volume to the device being implanted. It would also be desirable that such devices would controllably deliver their agents over both the short term (that is, the initial hours and days after treatment) and the long term (the weeks and months after treatment). It would also be desirable to provide relatively precise control over the delivery rate for the agents, drugs or bioactive materials, and to limit invasive control in effecting that delivery. This would be particularly advantageous in therapies involving the delivery of a chemotherapeutic agent to a particular organ or site without requiring reinsertion or additional insertion to the patient through an intravenous catheter (which itself has the advantage of reducing the amount of agent needed for successful treatment). This would reduce the trauma to the patient and reduce additional invasion of the patient. A wide variety of therapies can be similarly improved by the practice of this methodology. Of course, it would also be desirable to avoid degradation of the agent, drug or bioactive material during its incorporation on or into any such device.

Problems experienced with the use of pumps, structural implants, pacemakers, defibrillators, and catheters, particularly catheters designed for urinary tract infections or indwelling vascular catheters such as those used in patients receiving long term chemotherapy for malignancies or antimicrobials for persistent infections present a significant risk in patients with an indwelling catheter. Although many such infections are asymptomatic, they are sometimes serious and can result in prolonging the length of stay and increasing the cost of hospital care. Bacteria are believed to gain access to the catheterized bladder either by migration from the collection bag and/or catheter or by ascending the periurethral space outside the catheter. It has been found that by coating catheters with silver or silver oxide reduced the incidence of catheter associated bacteriuria. Silver is known to possess antibacterial properties and is used topically either as a metal or as silver salts. It is not absorbed to any great extent and the main problem associated with the metal is argyria, a general gray discoloration. Although silver is an effective topical antibacterial agent, it tends to act only on bacteria in direct contact with the surface and is subject to chemical reactions such as oxidation, which reduce its long term effectiveness.

Additionally, where release of the antibacterial agent from a coating is solely by mass transfer release by elution or migration out of a coating, drug is unnecessarily released during movement to the implantation site. At a minimum, this drug is wasted during implantation, or in the case of highly active agents, it is released to a region where that drug is not needed.

U.S. Pat. No 5,418,130 describes a method for inactivating viral and/or bacterial contamination in blood cellular matter, such as erythrocytes and platelets, or protein fractions. The cells or protein fractions are mixed with chemical sensitizers and irradiated with, for example, WV, visible, gamma or X-ray radiation. In particular, quaternary ammonium or phosphonium substituted, halo-psoralen compounds are described as being useful. This system is for use on solutions or dispersions of cells or the like and is not described for application on medical devices.

A typical drug delivery system with a biodegradable release layer is shown by U.S. Pat. No. 6,342,250. U.S. Pat. No. 6,251,136 describes a method of forming a release catheter comprising a method for coating a stent, comprising the steps of: providing a stent; applying a base layer of sticky material to selected surfaces of said stent; applying pharmacological agent in micronized, dry form to selected surfaces coated by said base layer; and applying a membrane forming polymer coating through which said pharmacological agent is able to diffuse to all surfaces of said stent.

U.S. Pat. No. 4,723,950 by Lee relates to a microbicidal tube which may be incorporated into the outlet tube of a urine drainage bag. The microbicidal tube is manufactured from polymeric materials capable of absorbing and releasing anti-microbial substances in a controllable sustained time release mechanism, activated upon contact with droplets of urine, thereby preventing the retrograde migration of infectious organisms into the drainage bag. The microbicidal tube may be produced by one of three processes: (1) a porous material, such as polypropylene, is impregnated with at least one microbicidal agent, and then coated with a hydrophilic polymer which swells upon contact with urine, causing the leaching out of the microbicidal agent; (2) a porous material, such as high density polyethylene, is impregnated with a hydrophilic polymer and at least one microbicidal agent; and (3) a polymer, such as silicone, is compounded and co-extruded with at least one microbicidal agent, and then coated with a hydrophilic polymer. A broad range of microbicidal agents are disclosed, including chlorhexidine and triclosan, and combinations thereof. The purpose of Lee's device is to allow the leaching out of microbicidal agents into urine contained in the drainage bag; similar leaching of microbicidal agents into the bloodstream of a patient may be undesirable.

U.S. Pat. No. 6,168,601 shows a system utilizing the eutectic forming ability of related drugs to control release. Biologically active materials are provided in a cylindrical carrier medium with better control over the rate of delivery and length of time of delivery by providing a carrier having dissolved or dispersed therein at least two compounds having a common biologically active nucleus, but with different solubility parameters. The combination of the two different variants of the same drug with different solubility parameters provides the material with control over the rate of release of the compounds (by varying the proportions of the variants) and most importantly, extending the useful life of the device by enabling release of effective levels of the compounds over a longer period of time. The cylindrical carrier medium, comprised of silicone, further includes a tail, a skirt, or a rate-limiting membrane.

U.S. Pat. No. 5,091,442 by Milner relates to tubular articles, such as condoms and catheters, which are rendered antimicrobially effective by the incorporation of a non-ionic sparingly soluble antimicrobial agent, such as triclosan, The tubular articles are made of materials which include natural rubber, polyvinyl chloride and polyurethane. Antimicrobial agent may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. No. 6,224,579 discloses a method of producing a non-infecting medical article by imbuing the device in a solution containing synergistic amounts of two antibiotics. That article comprises a medical article prepared by exposing a polymer-containing medical article, for an effective period of time, to a treatment solution comprising between about 0.3 and 1.5 percent of a silver salt and between about 0.1 and 20 percent triclosan, where the treatment solution and the medical article do not contain chlorhexidine or a chlorhexidine salt.

Improved coatings and control of drug delivery is desired for medical devices.

SUMMARY OF THE INVENTION

The present invention relates to medical devices that are inserted or implanted into patients and that have antimicrobial coatings that controllably release free radicals into the vicinity of the device. These devices may have coatings that alter their rate of flow release or elution release of an antibacterial agent from a coating on the device upon immediate, local or external stimulation or external activation. By immediate is meant that the coating or element is itself heatable or responsive to radiation (e.g., Infrared responsive, RF responsive, etc.), local means that an adjacent element may generate the heat or accept radiation emission and convey the energy to the layer or element to stimulate the release of the free radical, and external activation includes a signal from a distal control to mechanically alter the size of an opening, or cause a stretching of elongation of the element to open pores or holes. The coating should therefore be responsive to immediate, local or external control such as by heating (e.g., by electrical resistance where an external wire is present on the device) or responsive to external RF [radio frequency] stimulus, sonic control [e.g., to disrupt a coating or to activate a battery driven circuit in the system], local radiation stimulation or activation and the like. By having control of the release rate, and in some structures without invasion of the patient by mechanical means in addition to the device itself, the release rate can be in response to need at the implant site. The class of compounds to be released are free radical compounds, compounds that release free radicals upon immersion or stimulation, the free radicals acting as the antibacterial agent. Semiconductor materials capable of emitting radiation (e.g., UV radiation that can be generated internally from the semiconductor to activate free radicals) may be used to control release of free radicals in a layer responsive to the emissions or temperatures that can be generated by the semiconductor.

DETAILED DESCRIPTION OF THE INVENTION

Figure 1:
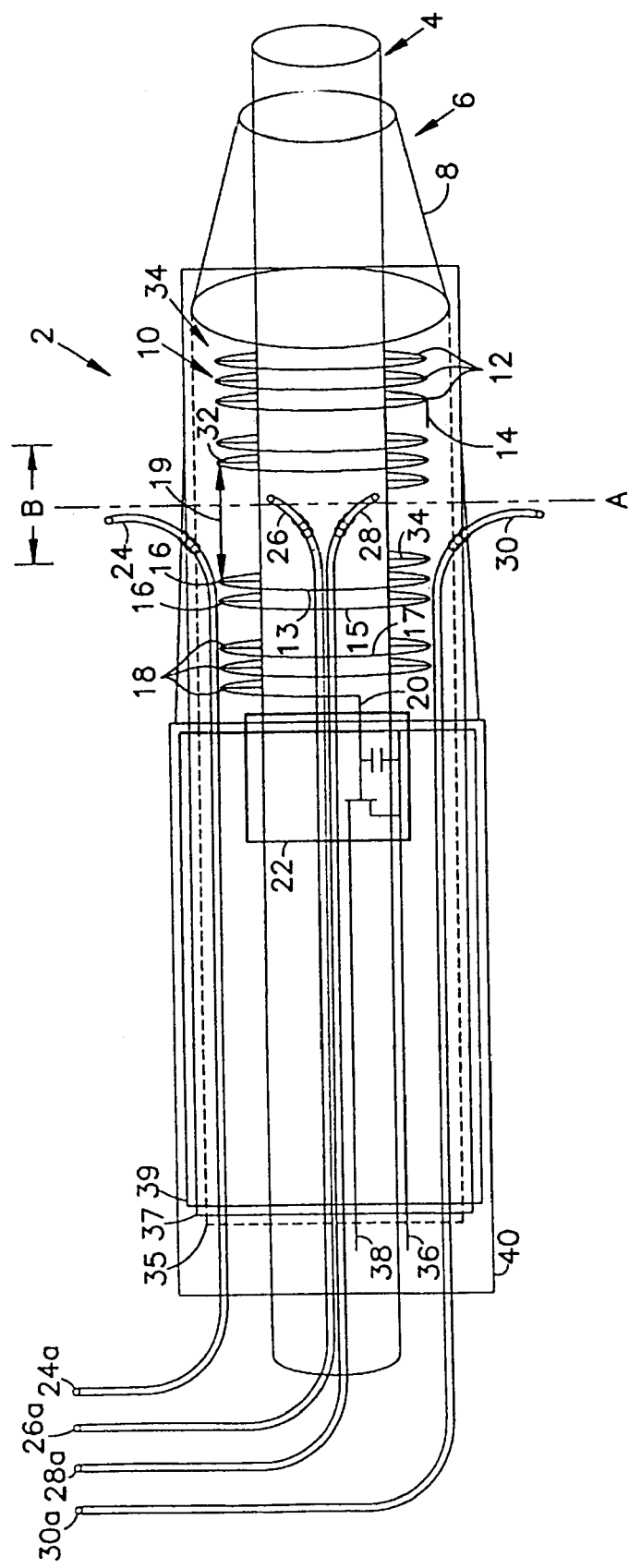
FIG. 1 shows a cutaway view of a catheter providing free radicals according to an aspect of the invention.

Over the past few years, free radicals have been implicated in all sorts of diseases. Every health supplement and face cream seems to include some protection against them—but what are they and, more importantly, what do they do? We first need to go back to basic level chemistry to understand what a free radical is. The chemical bonds that hold atoms together to make molecules contain pairs of electrons. For example, there are two electrons in each of the bonds holding the hydrogens of water to the oxygen. The two electrons act to stabilize the bond between the atoms. However, some molecules, especially those containing oxygen, can easily gain an extra one of these bonding electrons. As this electron is not paired with any other electrons, it makes the molecule very reactive. In a sense this molecule or atom with the extra, available electron is a molecule with a free chemical bond. This is essentially what a free radical is—a molecule containing unpaired electrons. This molecule will steal electrons from other molecules in order to pair its lone electron. In stealing this electron the structure of the electron-donating molecule may be changed or even turned into a free radical itself. Free radicals are generated by all sorts of different processes in the body. Approximately 5% of the oxygen that our cells use to burn sugars to release energy is lost as oxygen free radicals. UV light, cigarette smoke, and various other agents generate free radicals. White blood cells deliberately produce free radicals to kill invading bacteria. Free radicals can destroy enzymes, make proteins brittle, make cells leaky, cause cholesterol to become stuck in arteries and mutate DNA. Much of the process of ageing appears to be due to a very slow but steady wearing out of the body by free radical damage.

The body deals with free radicals either by using antioxidant enzymes, which degrade the radicals back to harmless water and oxygen, or with chemicals called antioxidants, which react with and neutralize the radicals. Vitamin C and vitamin E are the two most important antioxidants within the body. Vitamin E neutralizes radicals in the fats and oils of our body while vitamin C protects the water-soluble biomolecules.

Free radicals are relatively free from controversy in the medical field with respect to their toxicity, effectiveness, and long term effects. Although free radicals in solution are recognized as fighting or killing bacteria or viruses, much literature addresses the presence of free radicals in the body as unhealthy, contributing to cell deterioration, especially skin and tissue aging. A great deal of commercial literature focuses on the increase of antioxidants in diets to reduce the amount of free radicals in human blood streams to reduce aging effects. There is still incontrovertible evidence that free radicals in solution have a direct and immediate effect on disabling or killing bacteria and viruses. However, except for ozonation, there appears to be little effort that has been made in the direction of finding any useful method for applying free radicals to human therapy, except for the natural free radical generations effected by the body as part of its immune response.

Free radicals are atoms or groups of atoms with an unpaired valence electron. Free radicals can be produced by photolysis or pyrolysis in which a bond is broken without forming ions (e.g., hemolytic fission). The presence of the unpaired electrons causes free radicals to be highly active. Free radical generating compounds, especially those that are responsive to light and/or heat to generate the free radicals are especially well known in the photocatalytic art. Among the many types of free radical generating initiators known in the polymer art are triazines, s-triazines, quaternary ammonium compounds and salts; halogen releasing compounds; diazonimum salts, iodonium salts (especially diary iodonium salts), phosphonium salts (especially triaryl phosphonium salts), sulfonium salts (especially triaryl sulfonium salts), biimidazoles, benzophenones, and the like. Some of these materials are quite stable in aqueous environments, generating the free radicals only upon thermal or photoinitiation. Other classes of free radical generating compounds more typically known in the medical environment as a treatment for in vitro liquid supplies are fibrates (e.g., fenofibrate); NSAIDS such as benoxaprofen, carprofen, ketoprofen, naproxen, suprofen, Tiaprofenic acid; Germicides such as Bithionol, buclosamide, fenticlor, hexachlorophene, tetrachlorosalicylanilide, and triclosane; tetracyclines such as demeclocycline, doxycycline and tetracycline; quinolones such as cyprofloxacin, fleroxacin, lomefloxacin, nalidixic acid, and ofloxacin; psoralens such as bergamot oil, 5hydroxypsoralen, isopsoralen, 5-methoxypsoralen, 8-methoxypsoralen, and trimethylpsoralen; diphenhydramine, thiazides, sulfonylureas; azines such as chlorpromazine, and promethiazine. The use of brominated or halogenated psoralens is particularly useful in activation in the practice of the invention, either as pure coatings or dissolved or dispersed in polymeric coatings. Other types of intercalators may be utilized besides the psoralens and substituted psoralens such as those listed below. These intercalators may be used to target viruses or other blood contaminants, or cancer cells. Thus, halogenated or metal atom-substituted derivatives of the following compounds may be utilized as sensitizers: dihematoporphyrin esters, hematoporphyrin derivatives, benzoporphyrin derivatives, hydrodibenzoporphyrin dimaleimade, hydrodibenzoporhyrin, dicyano disulfone, tetracarbethoxy hydrodibenzoporhyrin, tetracarbethoxy hydrodibenzoporhyrin dipropionamide; and the like. The above compounds in their non-halogenated or non-metal atom substituted forms are disclosed in U.S. Pat. Nos. 4,649,151, 4,866,168, 4,883,790, 5,053,423 and 5,059,619, incorporated by reference herein. When modified with halogen atoms or metal atoms, the above-identified classes of compounds may be sensitized with electromagnetic radiation, including visible light. Semiconductors such as titanium dioxide and zinc oxide also produce free radicals upon UV and visible light exposure, and are preferred sources of free radicals in compositions used in the present invention.

Polymeric compositions are often used as coatings on medical devices, such as catheters or stents, as shown in U.S. Pat. No. 5,964,705, either as the structural material for the device or as an insulating or protective coating. Such medical devices, where the polymer is formed by a free radical polymerization process, may have residual free radical polymerization catalyst present in the polymer coating. The concentration of such free radical catalysts in polymers is typically on the order of 1–3% by weight. Literature citing extreme ranges of free radical catalysts may indicate levels as high as 10% by weight, but these are truly unrealistic amounts added to provide broad ranges of protection for purposes of legal disclosure. Even at those levels, and particularly where the inclusion in the polymer does not provide them in an active state or enable them to be come active, such low levels of free radical polymerization catalysts would not be a sufficiently high concentration of materials to maximize antibacterial activity according to the practice of the invention, and such activity has never been reported in the literature.

The invention encompasses various devices, including a medical device for insertion into a patient, the device having a surface with a coating thereon or containing within its outermost layer, an antimicrobial amount of at least one compound that provides microbe suppressing free radicals into an aqueous environment in contact with the device upon external stimulation of the coating, layer or compound. The device may provide the coating releases an amount of free radicals upon heating that increases in a rate of release from the coating to an aqueous environment by at least 20% when heated from 37° C. to 50° C. The device may have the coating release an amount of free radicals upon sonication that increases in a rate of release from the coating to an aqueous environment by at least 20%. The device may be designed with the coating comprising at least 0.0001% by weight of compounds that release free radicals when in contact with an aqueous environment. The device may have the coating comprise at least 0.005% by weight of compounds that release an antimicrobially active amount of free radicals when in contact with an aqueous environment. The device may alternatively have the coating comprise at least 0.1% by weight of compounds that release an antimicrobially active amount of free radicals when in contact with an aqueous environment. The device may have the compound generate free radicals upon stimulation by electromagnetic radiation. The device may have the coating comprises at least 1.0% or at least 1.5% by weight of the compounds. The free radical releasing compound may comprise a quaternary salt or a compound that releases halogen free radicals. The coating or outer layer may comprise at least 0.005% by weight of compounds that release an antimicrobially active amount of free radicals when stimulated by heat or electromagnetic radiation. There may be an electromagnetic receiver that initiates heat generation in the device to elevate the temperature of the coating. A battery may electrically attached to said device to power heat generation, or a transmitting wire is electrically attached to said device to power heat generation from an outside power source.

The invention may be alternatively described as medical device for insertion into a to patient, the device having a containing within its outermost layer an antibacterial amount of at least one compound that provides microbial-suppressing free radicals into an aqueous environment in contact with the device upon external stimulation. It ius preferred that the compound comprises $TiO_2$, $ZnO$, $SiO$, and other metal oxides either alone or in combination. The stimulation is preferably provided by infrared radiation, ultraviolet radiation or visible light. The antimicrobial agent may also be a photoactive compound.

In the practice of the present invention, coatings with free radical generating or free radical providing compositions should be present in the coatings on medical devices of the present invention as at least 0.0001% by weight of the coating because of the high activity of free radical materials. The coatings or compound contained within the coating on the device might make up only a fraction of the weight—possible as little as 0.0001%, at least 0.0005%, 0.001%, 0.005%, 0.01%, 0.05%, 0.1%, 0.5%, 1.0%, 2%, 5% by weight, at least 10% by weight, at least 12% by weight, at least 15% by weight, at least 20% by weight, at lest 25% by weight at least 30% by weight, up to solid coatings of 100% by weight of the free radical generator. Solid coatings are preferred but water immiscible oil-based coating may also be provided, although these can be rubbed off during insertion.

Coatings may be applied to the surfaces of the medical devices by any convenient method, including but not limited to dip coating, spray coating, iontopheresis, deposition coating, manual application, and the like. As the activity of the free radicals tends to be a surface phenomenon, or at least material is released from the surface, the coatings do not have to be thick to provide effective results. Coating of less than 0.5 microns can provide some significant activity, and layers thicker than 100 microns do not provide significantly additional effectiveness, although the thicker layers would provide a greater life and endurance. Therefore, the nominal thickness of 0.5 to 100 microns is merely a general range, and not exclusive of other thicknesses. Generally preferred ranges would be from 0.5 to 50 microns, 1.0 to 50 microns, 1 to 30 microns, 2 to 30 microns, or 2 to 25 microns.

The use of normal migration of free radical providing materials out of the coating is one method of providing local free radical antimicrobic activity. Providing thermally responsive or photoresponsive free radical generators requires some more substantive structure. For example, FIG. 1 shows a side view of a catheter 2. The catheter 2 has a drug delivery port 4 with a drug delivery tube 6, and narrowing tip 8. The catheter 2 is shown as layered, with layers 35, 37 and 39 to contain the structural elements of the catheter 2.

As an example of a structure with embodiments of the invention, this FIG. 1 will be described.

Layer 35 is a structural support layer in the catheter 2, supporting layer 37 that contains coils 12, 16, 18 and 32. Those coils 12, 16, 18 and 32 are powered through wires 36 and 38. These types of coils are traditionally used as RF responsive microcoils for generating a field of view under MRI (magnetic resonance imaging), but here with appropriate thickness, they can also be used as resistive wires. When sufficient current is passed through the coils 12, 16, 18 and 32, those coils would generate heat that could trigger free radical release in layers 39 and/or 40, either or both of which may comprise the free radical generating composition. Tubes 24, 24a, 26, 26a, 28, 28a, 30 and 30a represent microcatheters, light pipes, material delivery tubes and the like as designed into the structure. The figure shows microcatheters 24 and 30 as material 25 delivery ports. These material delivery ports 24 and 30 may deliver drugs locally during primary catheter treatment procedures and then be used to deliver ingredients that would actively cause release of free radicals in layer 40. Microcatheters 26 and 28 could be light pipes to deliver radiation towards layers 39 and/or 40 to cause photoinitiated release of free radicals from those layers 39 and/or 40. The release could be from the surface of layer 40 or from an interior wall of layer 39 so that free radicals are released into delivery tube 4 to diffuse out of that tube or to be forced out of the delivery tube 4. Component 22 may be a preamplifier, battery, RF receiving system, sonar-receiving system, or the like to control liquid flow through delivery tubes 26 and/or 28, or to control electrical flow into wire 20 and into the coils 16, 18, 10 and 32. Individual coils 13, 15, and 17 are shown, as is the spacing B and 19 between sets of coils. The coils are shown as two (32) or three (34) windings.

Coatings of materials can be provided in many variants and forms that can be externally activated. By the term "externally activated" it is meant that direction must be given from an outside source to initiate increased rates of release of the free radicals, and that even if there is some level of free radical release from the implanted or inserted structure, that rate may be increased upon an initiating signal from outside the patient or even with a sensor signaling function in the patient and communicatively attached to the device. The free radical materials are provided as a coating on at least a portion of the implanted device. The coating may have an initial release capacity for the free radicals of the coating composition and/or may have an additional and alternative antibacterial or anticlotting or other medically active compound that is released spontaneously during dwell of the implanted or inserted device. The free radical material must be deliverable by a signal function, as explained above. The coating may therefore be associated with a heating element, such as a resist heating element, a light emitting heating element (e.g., infrared emitter, or other radiation emitter with an absorber/thermal converter thermally connected to the free radical releasing layer), mass conductive heating element, or the like. The free radical providing layer may also be solvent activatable, where the introduction of a particular class of solvents or solutions to the region will leech and/or activate free radical materials from the coating. Alternatively, radiation projection onto the coating may cause release of free radicals as is the case with TiO2, free radical photonitiators, and coatings whose solubility change to release more dissolved or dispersed material when photoinitiated. Such release functions are well known in the photoimaging, printing and lithographic arts.

Prophetic Examples

A stent comprising an array of Titano® bars and crossbars providing flexibility and elastic memory that can undergo compression and expansion is dip coated into a solution comprising a bioinert polysiloxane polymeric binder and trial sulfonium tetrafluoroborate in a weight ratio of 10:90 in an organic solvent. The coating would be applied in an amount that upon drying would provide a 10 micron thick coating. A nickel/cadmium battery is electrically connected to the bars, with an intermediate RF receiver with switching capacity. The RF receiver is programmed to response to a preprogrammed signal so that upon receipt of the signal, a circuit is closed for a specified period of time (e.g., 1 minute) during which the battery heats the stent and the coating, the heat stimulating release of free radicals from the coating.

An alternative design places an ultraviolet radiation-emitting semiconductor underneath the coating and over the stent bars and cross-bars. The battery is electrically connected to the semiconductor so that upon being powered up, the semiconductor emits UV radiation, photoinitiating release of the free radicals.

A catheter is coated with $TiO_2$ and a UV emitting fiber optic is placed into the catheter at the skin's surface and fed down the catheter. The light source is turned on causing a photoinduced release of free radicals from the $TiO_2$. Alternatively, the catheter itself (with transparency through the structural material of the catheter (as in a radiation transparent window) can be used to transmit the light from an external source to the region of the free radical releasing composition.

What is claimed:

1. A medical device for insertion into a patient, the device having a surface with a coating thereon or containing within its outermost layer, an antimicrobial amount of at least one compound that provides microbe-suppressing free radicals into an aqueous environment in contact with the device upon external stimulation of the coating, layer or compound, wherein the coating releases an amount of free radicals upon heating that increases in a rate of release from the coating to an aqueous environment by at least 20% when heated from 37° C.to 50° C.

2. The device of claim 1 wherein the compound is selected from the group consisting of triazines, phosphonium salts, iodonium salts, sulfonium salts, biimidazoles, benzophenones, fibrates; benoxaprofen, carprofen, ketopofen, naproxen, suprofen, Tiaprofenic acid, bithionol, buclosamide, fenticlor, hexachlorophene, tetrachlorosalicylanilide, triclosane, tetracylclines, quinolones, lomefloxacin, nalidixic acid, ofloxacin, psoralens, diphenhydramine, thjazides, sulfonylureas, and azines.

3. The device of claim 2 wherein the coating comprises at least 0.1% by weight of compounds that release an antimicrobially active amount of free radicals when in contact with an aqueous environment.

4. The device of claim 2 wherein the coating comprises at least 0.005% by weight of compounds that release an antimicrobially active amount of free radicals when stimulated by heat or electromagnetic radiation.

5. The device of claim 1 wherein the coating releases an amount of free radicals upon sonication that increases in a rate of release from the coating to an aqueous environment by at least 20%.

6. The device of claim 1 wherein the coating comprises at least 0.00011% by weight of compounds that release free radicals when in contact with an aqueous environment.

7. The device of claim 6 having an electromagnetic receiver that initiates heat generation in said device to elevate the temperature of the coating.

8. The device of claim 7 wherein a battery is electrically attached to said device to power heat generation.

9. The device of claim 6 wherein a transmitting wire is electrically attached to said device to power heat generation from an outside power source.

10. The device of claim 1 wherein the coating comprises at least 0.005% by weight of compounds that release an antimicrobially active amount of free radicals when in contact with an aqueous environment.

11. The device of claim 10 wherein the free radical releasing compound comprises a compound that releases halogen free radicals.

12. The device of claim 1 wherein the compound generates free radicals upon stimulation by electromagnetic radiation.

13. The device of claim 1 wherein the coating comprises at least 1.0% by weight of the compounds.

14. The device of claim 1 wherein the coating comprises at least 1.5% by weight of the compounds.

15. The device of claim 1 wherein the free radical releasing compound comprises a compound that releases halogen free radicals.

16. The device of claim 1 wherein the coating comprises at least 0.005% by weight of compounds that release an antimicrobially active amount of free radicals when stimulated by heat or electromagnetic radiation.

* * * * *